United States Patent [19]

Hesselgren

[11] 4,232,784
[45] Nov. 11, 1980

[54] STAND FOR INSTRUMENTS FOR MEDICAL USE

[76] Inventor: Sven-Gunnar Hesselgren, Kummelvägen 19, S-161 39 Bromma, Sweden

[21] Appl. No.: 18,627

[22] Filed: Mar. 8, 1979

[30] Foreign Application Priority Data

Mar. 20, 1978 [SE] Sweden ............................... 7803160

[51] Int. Cl.³ .......................... A61L 2/26; A61L 2/06; B65D 81/26; C23F 11/00
[52] U.S. Cl. .................... 206/210; 206/63.5; 206/369; 206/370; 422/8; 422/40; 422/300; 422/310; 433/77; 433/229
[58] Field of Search .................. 422/7, 8, 9, 294, 297, 422/300, 310, 10, 40; 206/207, 208, 210, 369, 370, 63.5; 433/77, 229

[56] References Cited

U.S. PATENT DOCUMENTS

| | | | |
|---|---|---|---|
| 2,707,551 | 5/1955 | Shnitzler et al. ...................... | 422/8 X |
| 2,870,905 | 1/1959 | Holohan .......................... | 206/208 X |
| 3,642,998 | 2/1972 | Jennings ............................. | 206/207 |

FOREIGN PATENT DOCUMENTS

| | | | |
|---|---|---|---|
| 584999 | 9/1933 | Fed. Rep. of Germany .......... | 206/208 |
| 235820 | 4/1945 | Switzerland ............................ | 206/208 |
| 918570 | 2/1963 | United Kingdom ..................... | 206/207 |

*Primary Examiner*—Barry S. Richman
*Attorney, Agent, or Firm*—Lerner, David, Littenberg & Samuel

[57] ABSTRACT

A stand for instruments of metal for use in the field of medicine, particularly odontology, comprising a body composed of a large number of sheets of a liquid impregnatable paper material. The sheets are arranged vertically close together so that the instruments are insertable by their operating ends between the sheets to be retained there during the sterilizing process and are thus stored easily accessible for subsequent clinical work. The sheets of paper are impregnated with a corrosion inhibitor to protect the instruments at least during a sterilizing process.

4 Claims, 2 Drawing Figures

STAND FOR INSTRUMENTS FOR MEDICAL USE

BACKGROUND OF THE INVENTION

The present invention relates to a stand for instruments of metal, such as root canal files, nerve extractors, drills and the like, for use in the field of medicine, particularly odontology.

Various materials and instruments with extremely specific properties and design are used for root filling or endodontic treatment.

Examples of such instruments are root canal files and nerve extractors which are characterized, inter alia, by comparatively slim dimensions, but upon which, nevertheless, considerable demands for strength are placed. Other properties are great flexibility to enable the finely branched anatomy of the root canals to be followed. Another necessary property of the instruments is sharp edges to enable efficient mechanical clearing of the walls of the root canal.

In all endodontical treatment all operations must be performed using aseptic methods in order to prevent the spread of infection.

This means, for instance, that the instruments used must be sterilized in a reliable manner, i.e. either by means of autoclave sterilization in saturated water vapour at 120°-130° C. for 10-20 minutes or by means of dry sterilization at 180° C. with a sterilization time of 90 minutes. It has long been recognized that treating root canal instruments with conventional sterilizing techniques causes considerable damage to the instruments, primarily due to corrosive attacks which deteriorate the sharpness of the edges and greatly increase the risks of the instruments breaking when used.

In view of the high demands placed on their cutting ability, root canal instruments are preferably made of carbon steel (compare scalpels). However, carbon steel is attacked by oxygen in the air and even more so in a moist heat such as that occurring in autoclave sterilization.

The relatively high temperature required for dry sterilization also affects the carbon steel instruments unfavourably, increasing the brittleness of the material, deteriorating the edge sharpness and causing oxidation deposits on the surface of the instruments.

However, in comparison with autoclave sterilization, sterilization with dry heat causes less destruction to these instruments. Since it is becoming more and more usual to change over to autoclave sterilization in the odontological field too, the problem of damage to the instruments is being accentuated.

In order to avoid the unfavourable effects caused by the inescapable sterilization procedures described, the root canal instruments have been surface treated, for instance by chromium-plating them at the manufacturing stage. Admittedly this provides better protection against corrosion but on the other hand the edge loses its sharpness due to the surface treatment.

Other methods of solving the problem are to provide the instruments with a thin coating of some corrosion inhibitor immediately prior to sterilization, either by spraying the instruments with an inhibitor solution or by dipping them in the solution. With autoclave sterilization it is also possible to add a water soluble corrosion inhibitor to the water in the autoclave, which is then vaporized together with the water upon heating.

However, none of the proposed solutions have given a satisfactory result when applied to root canal instruments, possibly because it is impossible to maintain a sufficient concentration of the corrosion inhibitors throughout the sterilization cycle.

The instruments must be placed in special file stands to enable them to be gripped directly with thumb and index finger without contaminating the rest of the instruments. Placing the instruments in file stands of metal also contributes to increased corrosion due to the electrolytic action which occurs upon contact between different metals.

SUMMARY OF THE INVENTION

However, the practice of the present invention has shown that the difficulties mentioned above can be overcome easily and is also pleasant for the user from the point of view of treating technique.

The invention is characterized in that the instrument stand comprises a body composed of a large number of sheets of a liquid impregnatable paper material, the sheets being arranged vertically close together, said instruments being insertable by their points or operative ends between said sheets to be retained there during a sterilization process and are thus stored easily accessible for subsequent clinical work, and that said sheets of paper are impregnated with a corrosion inhibitor to protect the instruments at least during a sterilization process.

The invention will be described further in the following with reference to the drawing in which.

Figure 1:
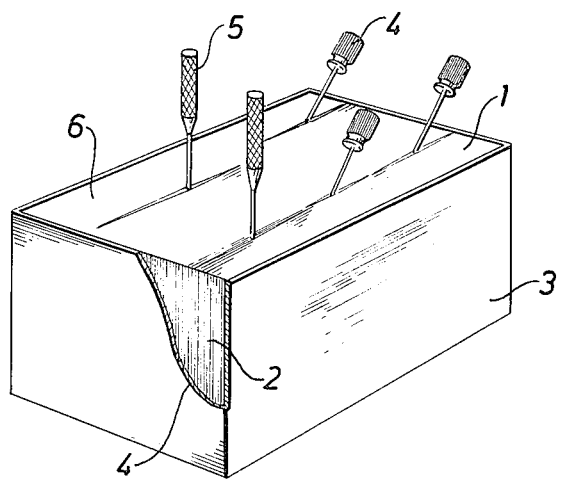
FIG. 1 shows an instrument stand according to the invention in perspective.

The device shown in the drawing consists of a block-shaped body 1 constructed of a large number of vertically placed sheets 2 of paper arranged close together and a means 3 holding the sheets together in a close surface to surface relation and stabilizing them. In the embodiment shown this means consists of a casing 4 of paper or some other suitable material which surrounds the sheets 2 in a stabilizing manner. However, it will be understood that such a means may also comprise pasting or pasted sheets or the like at both end sides of the body. A practical dimension for such a body has been found to be: height 3 cm, width 35 cm and length 6-8 cm.

Figure 2:
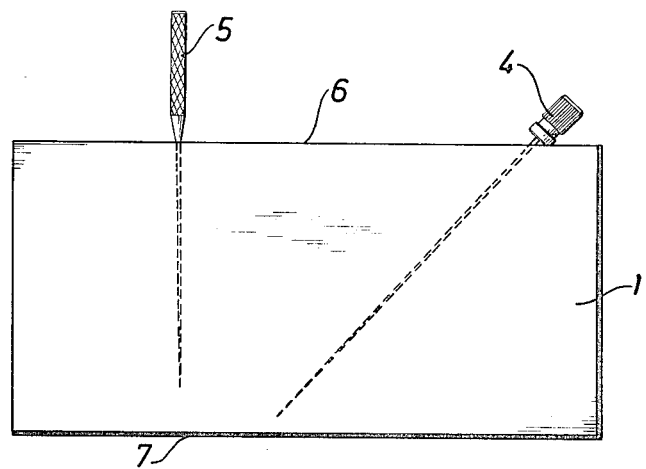
FIG. 2 shows the instrument stand from the longitudinal side.

This device thus serves as instrument stand in which it is easy to arrange and distribute root canal files 4, 5 and similar instruments in the desired number by sticking them in from the top side 6 between the tightly packed sheets of paper. Since the sheets are parallel in the longitudinal direction, fairly long instruments can also be inserted without protruding too much if they are inclined as shown in FIG. 2. This is a considerable advantage since the vertical space is limited in view of the fact that the complete set of instruments required during a treatment is usually laid on a standardized instrument tray with a removable lid of specific limited height. The instrument stand is preferably constructed so that the instruments can be inserted between the sheets from either of the two flat sides 6, 7, i.e. the stand can rest on any of said flat sides.

The sheets of paper from which the instrument stand is manufactured are impregnated with one or more corrosion inhibitors in suitable concentrations.

Due to the intimate contact between the metal instruments and the corrosion impregnated paper, the protection against the destructive factors during the entire sterilization cycle will be maximal.

After having been used a number of times, the instrument stand is considered expended and is therefore replaced by a new one. This ensures satisfactory protection against corrosion.

When carrying out a treatment the operator can easily find the desired root canal file or other instrument amongst the instruments arranged in the stand on the instrument tray.

When the first file has been used, the cleaning process is continued using the next size of file and so on until the root canal lumen has been satisfactorily prepared.

During this series of treatments it is therefore desirable to have access to a file stand where used files can also be replaced in a simple manner. The file stand according to the invention eliminates the need for time-consuming precision in placing instruments in the diminutive notches intended for them in conventional models of metal stands.

A re-used file will be automatically freed from collected grindings, known as dentine debris, from the previous cleaning, due to the friction against the paper laminates. This wiping process noticeably increases the grinding effect of the file. In methods used hitherto, this has been achieved by extra wiping on gauze or the like performed by the operator himself.

Due to the laminated structure of the instrument stand the water vapour can pass through the entire stand during the sterilization process thus eliminating the risk of pockets of air remaining which are unsterile or infected material which might jeopardize the result of the sterilization process. This risk does not exist with hot air sterilization since the conducted heat is the sterilizing factor.

Bacteriological sterility tests with samples of spores have confirmed that perfectly satisfactory sterility has been achieved by using accepted sterilizing methods and programs. The tests were performed as follows: A number of root canal files were infected with heat-resistant spores and thereafter placed in the instrument stand. An ordinary sterilization program for the usual instruments was performed after which the root files were transferred to bacteriological substrate for cultivation. The existance of growth was checked daily during an incubation period of in all 12 days. In no case was there any growth.

Known corrosion inhibitors which are accepted for use within medicine and odontology may be used. Among these may be mentioned primarily the group of amines, for instance cyclohexylamine, morpholine, dodecylamine, diethanolamine, triethanolamine and salts thereof, and benzoates and nitrites.

The block or instrument stand may preferably be placed in a frame of metal of such inner dimensions that the length corresponds to the length of the block, the height is the same as or somewhat less than the height of the block and the width is somewhat greater than the width of the block. The block is thus secured in the frame at the ends but since the frame is somewhat wider than the block there is space for the lateral expansion which the block undergoes during sterilization. The four-sided frame with vertical walls provides the desired stabilization and positions the block on the instrument tray besides acting as holder. The casing 3 may in this case be omitted.

I claim:

1. A stand for maintaining and sterilizing metallic medical instruments comprising a casing including an upper open face, a bottom face, and a pair of sidewalls, and a plurality of sheets of liquid impregnatable paper arranged in said casing in face-to-face contact so as to form a stack of sheets between said sidewalls of said casing with the sides of said stack of sheets communicating with said upper open face and said bottom face of said casing, said plurality of sheets of paper being impregnated with a corrosion inhibitor so that said instruments are insertable between said sheets from said upper open face of said casing in a manner such that said instruments may be stored therein, and further whereby the entire surface of said instruments inserted between said sheets in said casing is in contact with said sheets of paper impregnated with corrosion inhibitor and may be retained in such configuration during a sterilization process.

2. A stand according to claim 1 wherein the distance between said upper open face of said casing and said bottom face of said casing is less than the length of the longest instrument utilized but greater than the length of the smallest instrument utilized.

3. The stand of claim 1 surrounded by a frame.

4. The stand of claim 3 wherein said frame is made of metal.

* * * * *

UNITED STATES PATENT AND TRADEMARK OFFICE
CERTIFICATE OF CORRECTION

PATENT NO. : 4,232,784
DATED : November 11, 1980
INVENTOR(S) : Sven-Gunnar Hesselgren It is certified that error appears in the above-identified patent and that said Letters Patent are hereby corrected as shown below:

Column 2, line 46, "35" should read --3.5--.

Signed and Sealed this

Seventeenth Day of March 1981

[SEAL]

Attest:

RENE D. TEGTMEYER

Attesting Officer

Acting Commissioner of Patents and Trademarks